US010729880B2

(12) United States Patent
Kim et al.

(10) Patent No.: US 10,729,880 B2
(45) Date of Patent: Aug. 4, 2020

(54) PACKAGED INTRAVASCULAR MEDICAL DEVICE WITH VARIABLE VISCOSITY INTRAVENOUS LIQUID SOLUTION

(71) Applicant: Cook Medical Technologies LLC, Bloomington, IN (US)

(72) Inventors: Woong Kim, West Lafayette, IN (US); Kenneth Haselby, Battle Ground, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 53 days.

(21) Appl. No.: 15/877,560

(22) Filed: Jan. 23, 2018

(65) Prior Publication Data

US 2018/0214664 A1 Aug. 2, 2018

Related U.S. Application Data

(60) Provisional application No. 62/453,127, filed on Feb. 1, 2017.

(51) Int. Cl.
*A61M 25/00* (2006.01)
*A61B 50/30* (2016.01)
(Continued)

(52) U.S. Cl.
CPC ........... *A61M 25/002* (2013.01); *A61B 50/30* (2016.02); *A61F 2/0095* (2013.01); *A61M 5/36* (2013.01);
(Continued)

(58) Field of Classification Search
CPC ....... A61M 25/002; A61M 5/36; A61B 50/30; A61B 50/20; A61B 2050/3005; A61B 2018/00345; A61F 2/0095; A61F 2/95
(Continued)

(56) References Cited

U.S. PATENT DOCUMENTS

| 4,411,866 A | 10/1983 | Kanno |
| 4,881,562 A * | 11/1989 | Wright .................... A61F 2/00 134/110 |

(Continued)

FOREIGN PATENT DOCUMENTS

| CN | 101122557 | 6/2011 |
| WO | 2010054345 | 5/2010 |

OTHER PUBLICATIONS

Eun Young Park et al.; Carbon Dioxide Embolism During Laparoscopic Surgery; Yonsel Med J., May 2012; 53 (3):459-466; Published in US online. https://doi.org/10.3349/ymj.2012.53.3.459.
(Continued)

*Primary Examiner* — Steven A. Reynolds
(74) *Attorney, Agent, or Firm* — Liell + McNeil

(57) ABSTRACT

An intravascular medical device is prepared for shipping by being sealed within a sterile volume of a package. Prior to closing the package, an intravenous liquid solution is pumped into and through the medical device to displace all air bubbles. The liquid is pumped at sterilization temperatures corresponding to when the liquid has a low viscosity, but the liquid is chosen to have a relatively high viscosity at room temperatures corresponding to when the package is opened for use. The liquid solution remains adsorbed to the interior surfaces of the medical device at room temperature against a force of gravity. The strategy reduces the risk of air embolism when a medical device is put into use.

6 Claims, 2 Drawing Sheets

(51) Int. Cl.
*A61M 5/36* (2006.01)
*A61F 2/00* (2006.01)
*A61B 18/00* (2006.01)
*A61F 2/95* (2013.01)

(52) U.S. Cl.
CPC ....... *A61B 2018/00345* (2013.01); *A61F 2/95* (2013.01)

(58) Field of Classification Search
USPC .......................................... 206/364, 363, 438
See application file for complete search history.

(56) References Cited

U.S. PATENT DOCUMENTS

| | | | |
|---|---|---|---|
| 5,500,067 A | 3/1996 | Jenkner | |
| 5,681,740 A * | 10/1997 | Messier | A01N 1/02 206/438 |
| 6,140,144 A | 10/2000 | Najafi et al. | |
| 9,333,077 B2 | 5/2016 | Peter | |
| 2010/0072642 A1 | 3/2010 | Broad et al. | |
| 2013/0197455 A1* | 8/2013 | Zhang | A61M 25/00 604/265 |
| 2015/0335856 A1* | 11/2015 | Utas | A61M 25/002 206/210 |
| 2016/0000062 A1* | 1/2016 | Chen | A61M 5/002 435/1.3 |
| 2016/0346517 A1 | 12/2016 | Werneth et al. | |
| 2017/0340857 A1* | 11/2017 | Ryan | A61M 25/0111 |

OTHER PUBLICATIONS

Koan Sik Woo et al.; Characteristics of the Thermal Degradation of Glucose and Maltose Solutions; Prev. Nutr. Food Sci.; Jun. 2015; 20(2): 102-109; Published in US online. http://dx.doi.org/10.3746/pnf.2015.20.2.102.

Tilo Kölbel, MD, PhD et al.; Carbon Dioxide Flushing Technique to Prevent Cerebral Arterial Air Embolism And Stroke During TEVAR; Journal of Endovascular Therapy; 2016; vol. 23(2) 393-395. Published in US, Nov. 2016.

Philipp Kahlert, MD, Fesc et al.; Silent Cerebral Ischemia After Thoracic Endovascular Aortic Repair: A Neuroimaging Study; The Society of Thoracic Surgeons Published by Elsevier Inc.; 2014; pp. 53-58; Published in US, Worldwide web http://dx.doi.org/10.1016/j.athoracsur.2014.03.037.

Haulon et al.; Global Experience With An Inner Branched Arch Endograft; The Journal of Thoracic and Cardiovascular Surgery; vol. 148, No. 4, pp. 1709-1716. Published in US, Nov. 2016.

European Patent Office, European Search Report for Application No. 18275012.5, Published May 22, 2018, Munich Germany.

* cited by examiner

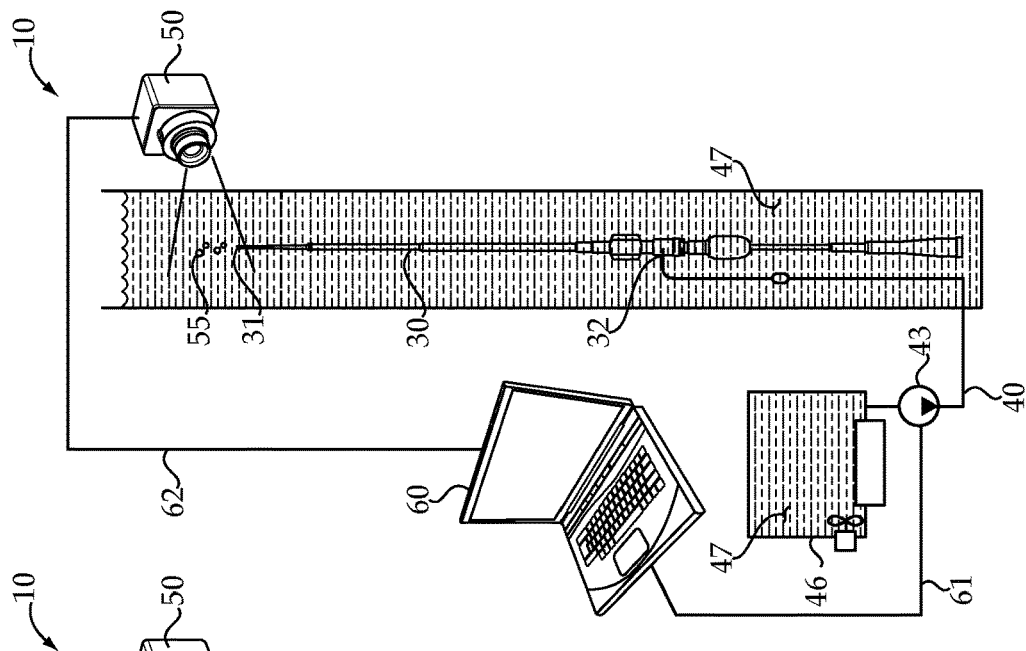
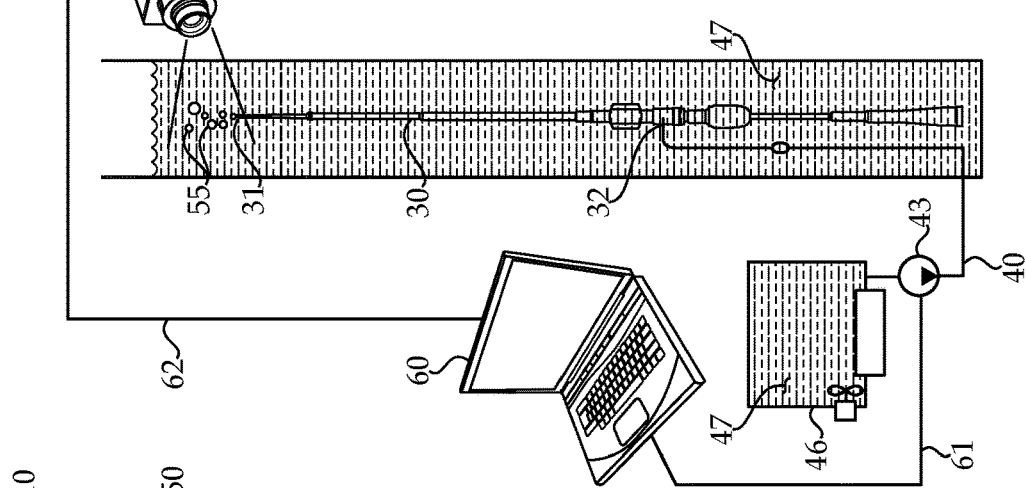
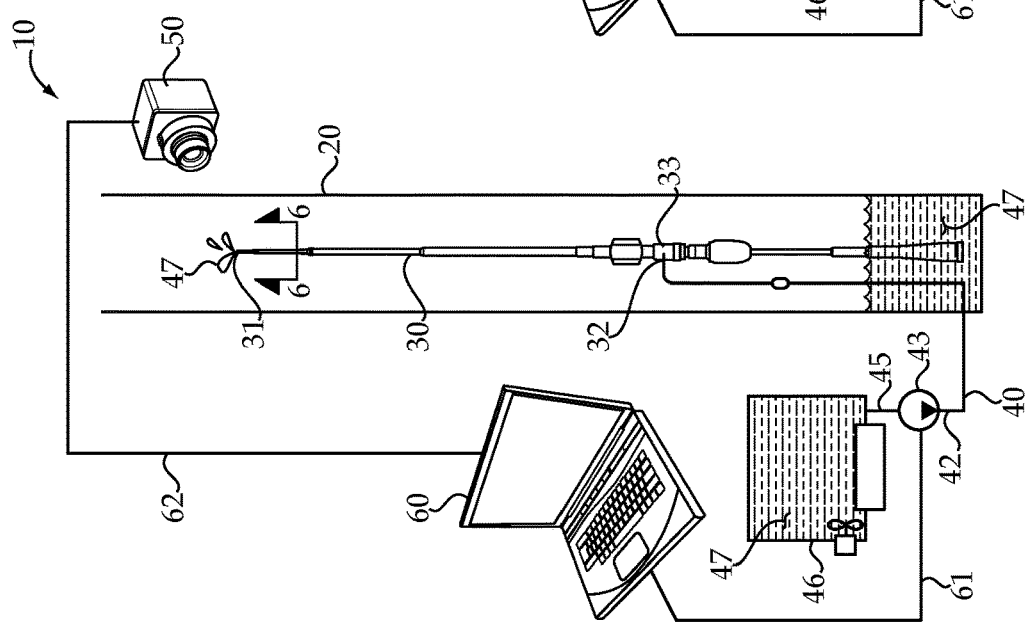

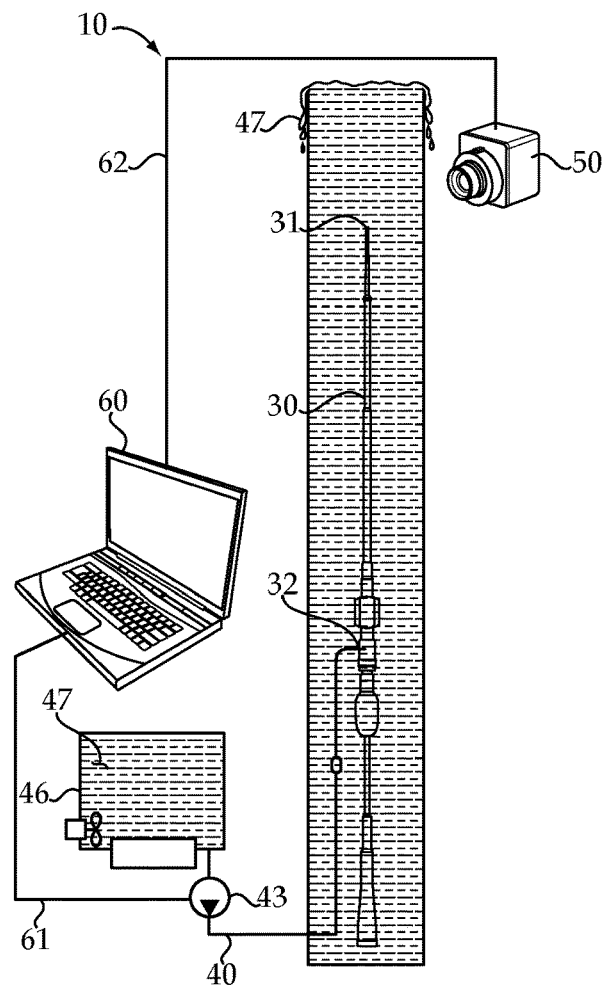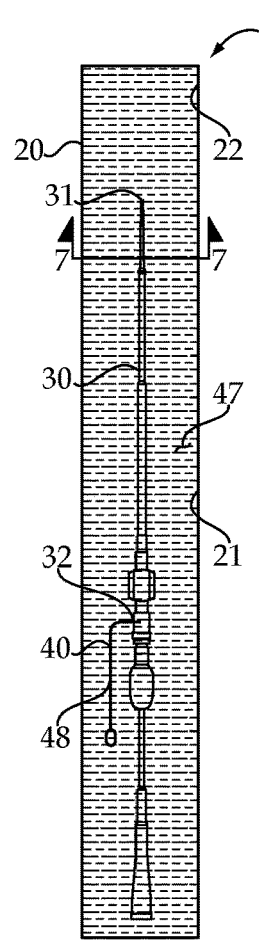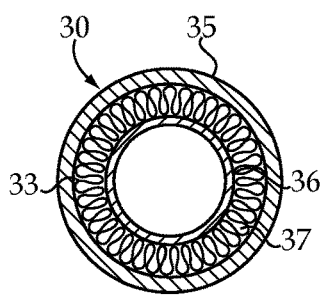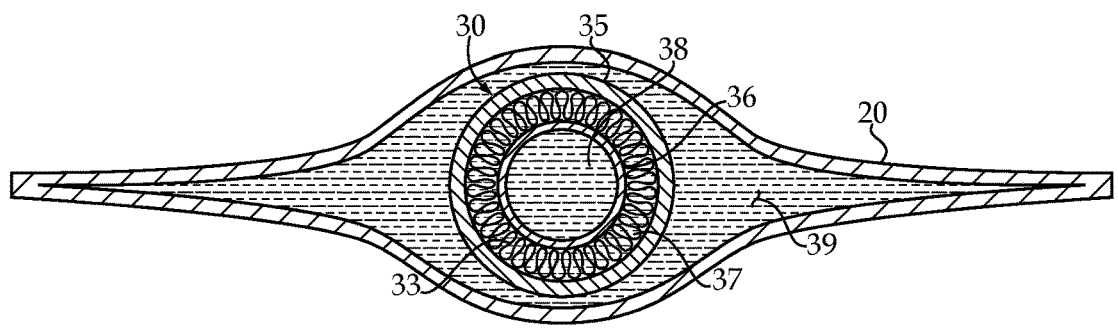

US 10,729,880 B2

PACKAGED INTRAVASCULAR MEDICAL DEVICE WITH VARIABLE VISCOSITY INTRAVENOUS LIQUID SOLUTION

TECHNICAL FIELD

The present disclosure relates generally to packaging of intravascular medical devices, and in particular to avoiding air embolisms by packaging the intravascular medical device with an intravenous liquid solution.

BACKGROUND

Air embolism caused by unintended air introduction into the circulatory system during a surgery can cause stroke in patients. This can occur when a small amount of gas trapped inside an endovascular medical device is introduced into the blood circulation during a procedure. In order to minimize the risk of air embolism, the current practice is to flush out the air by use of saline through a flush chamber to saturate the device with saline prior to introduction into the patient. Nevertheless, in practice, the saline flush method is known to be associated with a substantial percentage of clinical air embolism in endovascular cases. This is suspected because of unaccounted air is trapped in crevices and other difficult to flush locations within the medical device. There is currently no good data to know the lethal volume of air that can be passed into a patient's blood system without causing stroke.

The present disclosure is directed toward one or more of the problems set forth above.

SUMMARY OF THE DISCLOSURE

A packaged intravascular medical device includes a package that encloses a sterile volume. An intravascular medical device is wholly positioned in the sterile volume. An intravenous liquid solution is positioned in the sterile volume in contact with an internal surface of the intravascular medical device. The intravenous liquid solution has a low viscosity at a sterilizing temperature corresponding to when the package was closed, but a high viscosity at a room temperature when the package is opened for use of the intravascular medical device. The liquid solution remains adsorbed to the internal surface at the room temperature against a force of gravity.

In another aspect, an intravascular medical device packaging assembly includes a package that is open. An intravascular medical device is positioned in the package. A liquid supply line has one end fluidly connected to an interior volume of the intravascular medical device, and an opposite end connected to an outlet of a pump, which is positioned outside the package. A liquid supply reservoir is fluidly connected to an inlet of the pump. The liquid supply reservoir contains an intravenous liquid solution that has a low viscosity at a sterilizing temperature corresponding to when the intravenous liquid solution is pumped into the intravascular medical device by the pump prior to the package being closed, but a high viscosity at a room temperature when the package is opened for use of the intravascular medical device.

In still another aspect, a method of preparing an intravascular medical device for shipment includes displacing gas inside the intravascular medical device with an intravenous liquid solution pumped into the intravascular medical device at a sterilizing temperature corresponding to when the liquid solution is at a low viscosity. The intravascular medical device with the liquid solution is positioned into a sterile volume of a package. The package is sealed closed with the intravascular medical device wholly positioned in the sterile volume, and the liquid solution positioned in the sterile volume is adsorbed in contact with an internal surface of the intravascular medical device. The liquid solution has a high viscosity at room temperature when the package is opened for use of the intravascular medical device. The liquid solution remains adsorbed to the internal surface at the room temperature against a force of gravity when the intravascular device is removed from the sterile volume for use.

BRIEF DESCRIPTION OF THE DRAWINGS

FIG. 1 is a schematic view of an intravascular medical device packaging assembly at a first stage of a packaging procedure;

FIG. 2 is a schematic showing a later stage in the packaging procedure;

FIG. 3 shows still a later stage in the packaging procedure;

FIG. 4 is a schematic view toward the end of the packaging procedure;

FIG. 5 shows a schematic view of a packaged intravascular medical device that is prepared for shipment;

FIG. 6 is a sectioned view through the intravenous medical device as viewed along section lines 6-6 of FIG. 1, prior to injection of the intravenous liquid solution; and FIG. 7 is a sectioned view through the packaged and intravascular medical device as viewed along section lines 7-7 of FIG. 5.

DETAILED DESCRIPTION

Referring initially to FIG. 1, an intravascular medical device packaging assembly 10 schematically illustrates an initial set up for packaging an intravascular medical device prior to shipment. The packaging assembly 10 displaces trapped air bubbles in internal and external surfaces of the intravascular medical device with an intravenous liquid solution 47. As one example, and in reference briefly to the sectioned view of FIG. 6, the intravascular medical device may be any known device, such as a self expanding stent delivery system that includes an endovascular graft 33 compressed between a retractable sheath 35 and a catheter 36. The present disclosure seeks to saturate the interior space 37 with the intravenous liquid solution 47 at time of packaging in order to ensure that no air bubbles are present when the intravascular medical device 30 is later unpackaged for use. The packaging assembly 10 includes the intravascular medical device 30 positioned in a package 20, which is open. A liquid supply line 40 has one end 41 fluidly connected to an interior volume 37 of the intravascular medical device, such as via a flush port 32. An opposite end 42 of the liquid supply line 40 is fluidly connected to an outlet 44 of a pump 43, which is positioned outside of the package 20. A liquid supply reservoir 46 is fluidly connected to an inlet 45 of the pump. The liquid supply reservoir 46 contains an intravenous liquid solution 47 that has a low viscosity at a sterilizing temperature corresponding to when the intravenous liquid solution 47 is pumped into the intravascular medical device 30 by the pump 43 prior to the package 20 being closed. However, the intravenous liquid solution 47 is chosen as one that has a high viscosity at a room temperature when the package 20 is opened for use of the intravascular medical device in a clinical setting. The theory of the present disclosure is that by forcing the intravenous liquid solution 47 into the intravascular medical device, which may be oriented vertical at the time of filling as shown, displaces air from the interior space 37 in order to inhibit or reduce the possibility of air embolism when the intravascular medical device 30 is put into use.

The packaging assembly 10 may be partially controlled by a computer 60 in control communication with pump 43, such as via a communication line 61. The computer 60 may include a control algorithm that controls the action of pump 43 to effectively displace air within intravascular medical device 30 with the intravenous liquid solution 47. For instance, computer 60 may command pump 43 to vary its output and maybe change output pressure, such as via pulsing, to more effectively displace air in the hard to reach cracks and crevices that surround the intravascular graft 33 (FIG. 6). Computer 60 may also be in communication with a bubble detection device 50, such as via a communication line 62, in order to possibly add a closed loop control feature to the pump control algorithm executed by computer 60 during the filling process. Bubble detection device 50 may be a known optical device that is positioned to detect air bubbles 55 exiting through a tip 31 of the intravascular medical device 30 responsive to the intravenous liquid solution 47 being pumped into the intravascular medical device 30 by pump 43. For instance, as shown in FIG. 4, when the bubble detection device 50 communicates to computer 60 that no more air bubbles 55 are emerging from tip 31, the computer may discontinue operation of pump 43 and prepare package 20 for being sealed closed for shipment. In order to facilitate this monitoring of air bubbles emerging from tip 31, the intravascular medical device 30 in general, and the tip 31 in particular may be uncovered and exposed directly to an interior surface 21 (FIG. 7) of package 20.

Referring now to FIGS. 5 and 7, after the pre-flushing process is completed using the intravascular medical device packaging assembly 10, one arrives at a packaged intravascular medical device 25 that includes a package 20 that encloses a sterile volume 22. The intravascular medical device 30 is wholly positioned in the sterile volume 22 in a conventional manner. The intravenous liquid solution 47 is positioned in the sterile volume 22 in contact with interior surfaces 34 of the intravascular medical device 30. The intravenous liquid solution 47 is chosen to have a low viscosity at sterilizing temperatures, such as when packaging assembly 10 is in operation, corresponding to when the package 20 is closed, but have a high viscosity at a room temperature when the package 20 is opened for use of the intravascular medical device 30. As used in this disclosure, the sterilizing temperature will fall in the range of 65 to 148° C. Room temperature according to the present disclosure falls in the range of 16 to 22° C. As used in this disclosure, a ratio of high viscosity (room temperature) to low viscosity (sterilizing temperature) will be at least 5 for intravenous liquid solutions that fall within the scope of the present disclosure. Ordinary saline would not qualify as an intravenous solution 47 according to the present disclosure. However, the intravenous liquid solution 47 maybe partially made of saline in an amount chosen to adjust the overall viscosity of the intravenous liquid solution 47 to best serve the purposes of the present disclosure. Thus, and intravenous liquid solution 47 according to the present disclosure may be predominantly composed of a material selected from a group consisting of maltose, dextrose, a gelatin based blood volume expander and soybean oil emulsion. By choosing a liquid solution 47 that has a high viscosity at room temperatures, the viscosity might be chosen such that 99% of the intravenous liquid 47 is retained inside the medical device 30 while held vertically at room temperature. This strategy seeks to ensure that air bubbles 55 do not find their way into the device 30 under the force of gravity when the package 20 is opened and the medical device 30 is removed therefrom for use, but prior to being inserted into a patient's body. During transportation and during handling after the device 30 is removed from package 20 for use, the liquid solution 47 should remain inside the device 30 against the forces of handling and gravity. For instance, a viscosity on the order of 50 cP or more might be desirable. On the otherhand, when the device 30 is filled at the elevated sterilizing temperature, the viscosity could be something on the order of 1-10 cP so that its viscosity is low enough to fill every crevasse within device 30.

Preferably, the entire sterile volume 22 is free of gas bubbles in contact with the intravascular medical device 30. Thus, the intravascular medical device 30 may be completely immersed, inside and out, in the intravenous liquid solution 47 within the sterile volume 22 of package 20. As such, the combination of the intravascular medical device 30 and the liquid solution 47 may completely fill the sterile volume 22. As briefly discussed earlier, the tip 31 of the intravascular medical device 30 may be uncovered within the sterile volume 22 and exposed directly to the interior surface 21 of package 20. Some considerations that go into choosing an appropriate intravenous liquid solution 47 according to the present disclosure include whether the liquid has a low medial lethal dose (LD 50) for intravenous fluids that are already approved by at least one of the US Food and Drug Administration or the European Medicines Agency. In addition, the liquid solution 47 ought to have a good shelf life, maybe on the order of two or more years, and the viscosity at room temperature is preferably sufficiently high that the intravenous liquid solution does not substantially drip out of the medical device 30 during handling prior to insertion into a patient.

INDUSTRIAL APPLICABILITY

The present disclosure finds general applicability to the packaging of any intravascular medical device. The present disclosure finds specific applicability to intravascular medical devices that include difficult to reach cracks and crevices where air bubbles can become trapped even after the device is flushed with saline in a conventional manner prior to being inserted into a patient. The present disclosure finds specific application to intravascular medical devices that are used for the delivery of stent grafts, which are often compressed and define numerous small locations where air bubbles can become trapped prior to the stent graft being expanded in vivo.

Referring now to all of the figures, a method of preparing an intravascular medical device 30 for shipment utilizes the packaging assembly 10. Prior to initiation, or before what is shown in FIG. 1, the intravascular medical device 30 may be dry but positioned within an open package 20 and maybe oriented vertically with regard to gravity to possibly use gravitational forces to assist in displacing air bubbles 55 from within the medical device 30. Prior to initiating the movement of the intravenous liquid solution 47 into the medical device 30, the reservoir 46 maybe de-gassed in a known manner, such as under vacuum at a sterilization temperature to remove any defused gas and destroy fungus and bacteria. The intravenous liquid solution 47 maybe a mixture of one of the materials identified earlier that is mixed with saline to achieve some desired viscosity. These viscosity considerations include the fillability of the medical device 30 with the liquid solution 47 at an elevated sterilization temperature, such as 100° C. without thermal degradation. The liquid solution 47 should be chosen such that it mixes immediately with blood upon entry into the circulatory system of a patient and does not cause any blockage. When the medical device 30 is properly positioned in open package 20, the filling algorithm executed by computer 60 may be initiated. When this occurs, the gas inside the intravascular medical device 30 is displaced with the intravenous liquid solution 47 pumped into the intravascular medical device 30 at a sterilizing temperature corresponding to when the liquid solution 47 is at a low viscosity. This may be accomplished in part by connecting the flushing port 32 of the intravascular medical device 30 to a reservoir 46 of the intravenous liquid solution 47 and a pump 43. The pump pushes the intravenous liquid solution 47 into the intravascular medical device 20. Although it is conceivable that the internal surfaces of the medical device, 30 could be pre-flushed according to the present disclosure outside of package 20. The methodology of the present disclosure is preferably performed while the intravascular medical device 30 is positioned inside package 20. This strategy allows for excess intravenous liquid 47 that exits from medical device 30 at its opposite ends during the pre-flushing process to be contained within package 20, while also adhering to external surfaces of the medical device 30 exposed within package 20. During the pre-flushing process, as shown in FIG. 2, the bubble detection device 50 may detect a rate and/or volume of air bubbles 55 emerging from tip 31 and communicate that information to computer 60 via communication line 62. The pre-flushing algorithm being executed by computer 60 may respond by changing the output pressure from pump 43 in a manner that testing shows more effectively displaces air bubbles positioned in hard to reach locations within the medical device 30. For instance, computer 60 may command pump 43 to pulse output pressure and flow rate to achieve this end. As the process continues as shown in FIG. 3, one could expect the bubble detection device 50 to detect a gradual decrease in the numbers and overall volume of air bubbles 55 emerging from tip 31. Eventually, as shown in FIG. 4, the bubble detection device 50 may communicate to computer 60 but no more bubbles are emerging from the tip 31 of medical device 30, thus indicating that the pre-flushing procedure may be ready for termination. During this process, the sterile volume 22 within package 20 may completely fill and may overflow prior to the package 20 being sealed closed for shipment as shown in FIG. 5. Thus, the bubble detection device 50 may detect a cessation of gas bubbles escaping from tip 31, and computer 60 may respond by stopping operation of pump 43. In some instances where their is a desire to coat all exposed surfaces inside and out of the medical device 30, it may be desirable to overfill the sterile volume 22 with the intravenous liquid solution 47 prior to sealing the package 20 closed. Part of the closure of package 20 may include disconnecting the flushing port 32 of the medical device 30 from the reservoir 47 after all of the gas bubbles has been displaced. In some instances, this may include sealing a segment 48 of the liquid supply line 40 into the sterile volume 22 of the package 20 when it is sealed closed as shown in FIG. 5. It might also be desirable to apply a vacuum to sterile volume 22 at the time the package 20 is closed.

Because the liquid solution has a high viscosity at room temperatures, when the package 20 is opened for use of the medical device 30, the Practitioner can have greater confidence that the device 30 is ready to deploy with a lower risk of air embolism due to possible air trapped within the medical device 30 in general, and in and around an intravascular graft 33 in particular. Nevertheless, the device may also undergo a routine saline flushing procedure immediately prior to being put into use within a patient.

What is claimed is:
1. A packaged intravascular medical device comprising:
a package that encloses a sterile volume;
an intravascular medical device wholly positioned in the sterile volume;
an intravenous liquid solution positioned in the sterile volume in contact with an internal surface of the intravascular medical device;
wherein the liquid solution has a first viscosity at a sterilizing temperature corresponding to when the package was closed, but a second viscosity, which is higher than the first viscosity, at a room temperature when the package is opened for use of the intravascular medical device; and
wherein the liquid solution remains adsorbed to the internal surface at the room temperature against a force of gravity.
2. The packaged intravascular medical device of claim 1 wherein the intravascular medical device is completely immersed in the liquid solution.
3. The packaged intravascular medical device of claim 1 wherein the intravascular medical device and the liquid solution completely fill the entire sterile volume.
4. The packaged intravascular medical device of claim 1 wherein a tip of the intravascular medical device is uncovered within the sterile volume and exposed directly to an interior surface of the package.
5. A packaged intravascular medical device comprising:
a package that encloses a sterile volume;
an intravascular medical device wholly positioned in the sterile volume;
an intravenous liquid solution positioned in the sterile volume in contact with an internal surface of the intravascular medical device;
wherein the liquid solution has a first viscosity at a sterilizing temperature corresponding to when the package was closed, but a second viscosity, which is higher than the first viscosity, at a room temperature when the package is opened for use of the intravascular medical device;
wherein the liquid solution remains adsorbed to the internal surface at the room temperature against a force of gravity, and
wherein the liquid solution is predominantly composed of a material selected from a group consisting of maltose, dextrose, gelatin based blood volume expander and soybean oil emulsion.
6. A packaged intravascular medical device comprising:
a package that encloses a sterile volume;
an intravascular medical device wholly positioned in the sterile volume;
an intravenous liquid solution positioned in the sterile volume in contact with an internal surface of the intravascular medical device;
wherein the liquid solution has a first viscosity at a sterilizing temperature corresponding to when the package was closed, but a second viscosity, which is higher than the first viscosity, at a room temperature when the package is opened for use of the intravascular medical device;

wherein the liquid solution remains adsorbed to the internal surface at the room temperature against a force of gravity; and wherein the sterile volume is free of gas bubbles in contact with the intravascular medical device.

* * * * *